(12) United States Patent
Puri et al.

(10) Patent No.: US 10,639,273 B2
(45) Date of Patent: May 5, 2020

(54) PARTICLES FOR INJECTION AND PROCESSES FOR FORMING THE SAME

(75) Inventors: Sonali Puri, Ashland, MA (US); Robert E. Richard, Wrentham, MA (US); John E. O'gara, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2723 days.

(21) Appl. No.: 12/341,433

(22) Filed: Dec. 22, 2008

(65) Prior Publication Data

US 2009/0169627 A1 Jul. 2, 2009

Related U.S. Application Data

(60) Provisional application No. 61/009,459, filed on Dec. 28, 2007.

(51) Int. Cl.
  *A61K 9/00* (2006.01)
  *A61K 31/704* (2006.01)
  *A61K 9/50* (2006.01)

(52) U.S. Cl.
  CPC .......... *A61K 9/0019* (2013.01); *A61K 31/704* (2013.01); *A61K 9/5026* (2013.01); *A61K 9/5084* (2013.01)

(58) Field of Classification Search
  USPC ........................................................ 424/484
  See application file for complete search history.

(56) References Cited

U.S. PATENT DOCUMENTS

| | | |
|---|---|---|
| 5,840,387 A | 11/1998 | Berlowitz-Tarrant et al. |
| 6,352,682 B2 | 3/2002 | Leavitt et al. |
| 2003/0185895 A1 | 10/2003 | Lanphere et al. |
| 2003/0206864 A1 | 11/2003 | Mangin |
| 2004/0091543 A1 | 5/2004 | Bell et al. |
| 2004/0101564 A1 | 5/2004 | Rioux et al. |
| 2005/0095428 A1 | 5/2005 | Dicarlo et al. |
| 2005/0196449 A1 | 9/2005 | Dicarlo et al. |
| 2005/0281798 A1* | 12/2005 | Gong et al. .................. 424/94.3 |
| 2006/0067198 A1 | 3/2006 | Lewis et al. |
| 2006/0251697 A1 | 11/2006 | Li et al. |
| 2008/0045654 A1 | 2/2008 | Richard et al. |

FOREIGN PATENT DOCUMENTS

| | | |
|---|---|---|
| WO | 1999012577 | 3/1999 |
| WO | 2003082360 A1 | 10/2003 |
| WO | 2003090722 A3 | 11/2003 |
| WO | 2004014446 A1 | 2/2004 |
| WO | 2006093969 A3 | 9/2006 |
| WO | 2006093972 A3 | 9/2006 |
| WO | 2006138330 A3 | 12/2006 |
| WO | 2007090897 A1 | 8/2007 |

OTHER PUBLICATIONS

Lewis et al. DC Bead: In Vitro Characterization of a Drug-delivery Device for Transarterial Chemoembolization. J. Vasc. Interv. Radiol. 17 (2 Pt. 1), pp. 335-342 (2006).*
Lewis et al. Doxorubicin eluting beads—1: Effects of drug loading on bead characteristics and drug distribution. J. Mater. Sci.: Mater. Med. 18, 1691-99 (2007).*
Bilbao et al., J. Vasc. Interv. Radiol. 2008, vol. 19, pp. 1625-1638 (Year: 2008).*
Contour™ Embolization Particles, Boston Scientific, Mar. 2010, https://www.bostonscientific.com/content/dam/bostonscientific/pi/portfolio-group/embolization/contour/Resources/Contour%20DFU.pdf, accessed Jun. 5, 2018 (Year: 2010).*
Rasuli et al., J. Vasc. Interv. Radiol. 2008, vol. 19, pp. 42-46 (Year: 2008).*
Xu et al., Angewandte Chemie Int. Ed., 2007, vol. 46, pp. 4999-5002 (Year: 2007).*
Du et al., JACS, 2011, vol. 133, pp. 17560-17563 (Year: 2011).*
Schnnaljohann, Adv. Drug Deliv. Rev., 2006, vol. 58, pp. 1655-1670 (Year: 2006).*
C.M. Hassan et al., "Structure and Applications of Poly(vinyl alcohol) Hydrogels Produced by Conventional Crosslinking or by Freezing/Thawing Methods", Adv. Polym. Sci., vol. 153, (2000), pp. 37-65.
N.A. Peppas et al., "Hydrogels in Biology and Medicine: From Molecular Principals to Bionanotechnology", Adv. Mater., vol. 18, (2006), pp. 1345-1360.

* cited by examiner

*Primary Examiner* — Jeffrey S Lundgren
*Assistant Examiner* — Stephanie K Springer

(57) ABSTRACT

In accordance with one aspect of the invention, injectable particles are provided which comprise (a) a first group of injectable particles comprising first polymeric particles loaded with a first therapeutic agent and (b) a second group of injectable particles comprising second polymeric particles loaded with a second therapeutic agent. The first and second polymeric particles may be the same or different, and the first and second therapeutic agents may be the same or different. Other aspects of the invention pertain to methods of making such particles, to kits that comprise such particles, and to methods of treatment that employ such injectable particles.

3 Claims, 1 Drawing Sheet

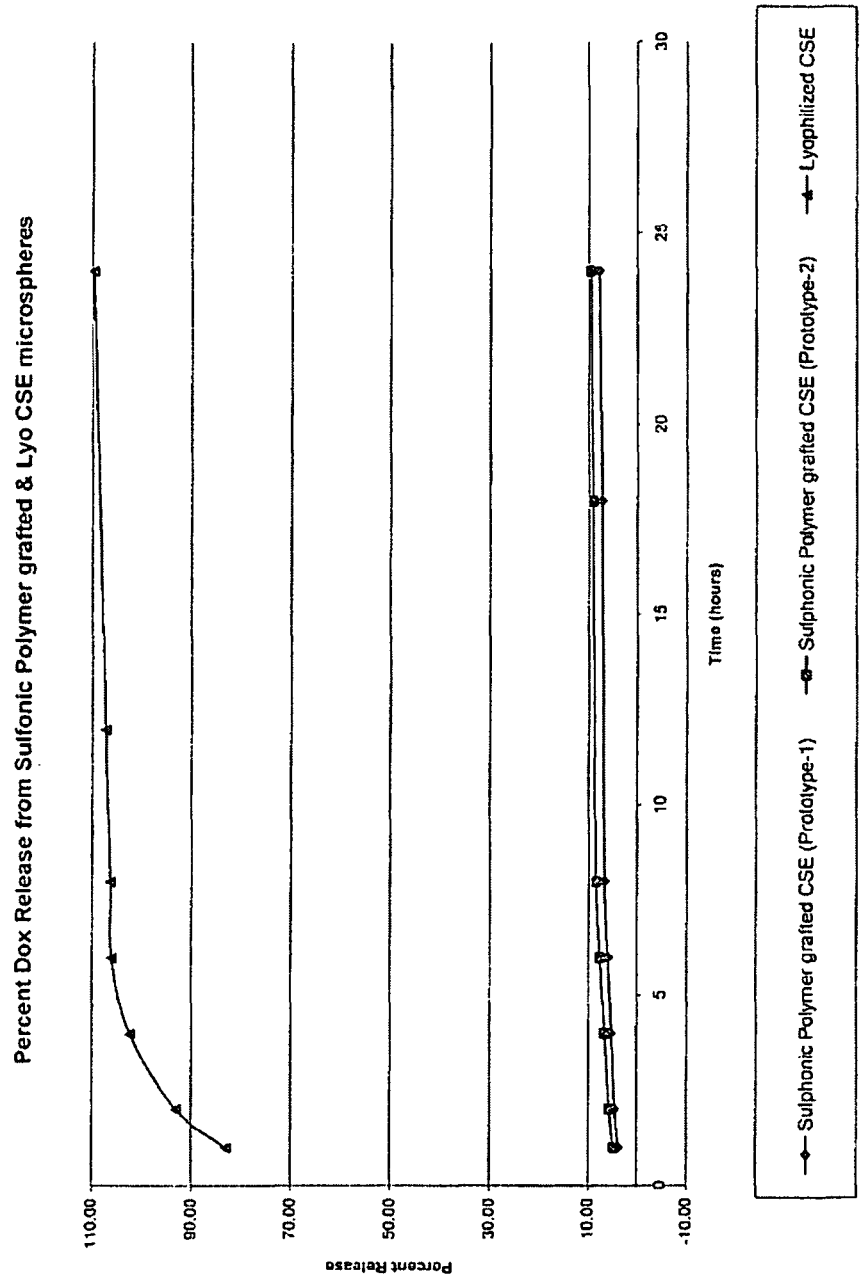

PARTICLES FOR INJECTION AND PROCESSES FOR FORMING THE SAME

STATEMENT OF RELATED APPLICATIONS

This application claims the benefit of U.S. Provisional Patent Application Ser. No. 61/009,459, filed Dec. 28, 2007, entitled "Particles For Injection And Processes For Forming The Same," which is incorporated herein by reference in its entirety.

FIELD OF THE INVENTION

The invention relates to particles for injection, to processes for forming the same, and to methods of using the same.

BACKGROUND OF THE INVENTION

Many clinical situations benefit from regulation of the vascular, lymphatic or duct systems by restricting the flow of body fluid or secretions. For example, the technique of embolization involves the therapeutic introduction of particles into the circulation to occlude blood vessels. Permanent or temporary occlusion of blood vessels is desirable for managing various diseases, disorders and conditions. For example, permanent or temporary occlusion of blood vessels can be used to either arrest or prevent hemorrhaging or to cut off blood flow to a structure or organ.

Various polymer-based microspheres are currently employed to embolize blood vessels. These microspheres are usually introduced to the location of the intended embolization through microcatheters. Current commercially available embolic microspheres are composed of biostable polymers. Materials commonly used commercially for this purpose include polyvinyl alcohol (PVA), acetalized PVA (e.g., Contour SE™ embolic agent, Boston Scientific, Natick, Mass., USA) and crosslinked acrylic hydrogels (e.g., Embospheres®, Biosphere Medical, Rockland, Mass., USA). Similar devices have been used in chemoembolization to increase the residence time of a therapeutic agent after delivery. In one specific instance, a therapeutic agent (doxorubicin) has been directly added to hydrogel microspheres (prepared from N-acrylamidoacetaldehyde derivatized polyvinyl alcohol copolymerized with 2-acrylamido-2-methylpropane sulfonate) such that it can be released locally after delivery (e.g., DC Bead™ drug delivery chemoembolization system, Biocompatibles International plc, Farnham, Surrey, UK). Other examples of commercially available microspheres include glass microspheres with entrapped radioisotopes (e.g., $^{90}Y$), in particular, TheraSpheres™, MDS Nordion, Ottowa, Canada and polymer microspheres that contain monomers that are capable of chelating radioisotopes ($^{90}Y$), in particular, SIR-Spheres®, SIRTex Medical, New South Wales, Australia.

It is also known to use polymer-based microspheres as augmentative materials for aesthetic improvement, including improvement of skin contour. Furthermore, polymer-based microspheres have also been used as augmentative materials in the treatment of various diseases, disorders and conditions, including urinary incontinence, vesicourethral reflux, fecal incontinence, intrinsic sphincter deficiency (ISD) and gastro-esophageal reflux disease. For instance, a common method for treating patients with urinary incontinence is via periurethral or transperineal injection of a bulking agent that contains polymer-based microspheres. The bulking agent is injected into a plurality of locations, assisted by visual aids, causing the urethral lining to coapt.

SUMMARY OF THE INVENTION

In accordance with one aspect of the invention, injectable particles are provided which comprise (a) a first group of injectable particles comprising first polymeric particles loaded with a first therapeutic agent and (b) a second group of injectable particles comprising second polymeric particles loaded with a second therapeutic agent. The first and second polymeric particles may be the same or different. Moreover, the first and second therapeutic agents may be the same or different.

Other aspects of the invention pertain to methods of making such particles, to kits that comprise such particles, and to methods of treatment that employ such injectable particles.

These and various additional aspects, as well as various embodiments and advantages of the present invention will become immediately apparent to those of ordinary skill in the art upon review of the Detailed Description and any Claims to follow.

BRIEF DESCRIPTION OF THE DRAWING

FIG. 1 is a plot of % release as a function of time for three groups of therapeutic-agent-containing particles.

DETAILED DESCRIPTION

In accordance with one aspect of the invention, injectable particles are provided which comprise first and second groups of therapeutic-agent-containing particles, in which the first group of therapeutic-agent-containing particles comprises first polymeric particles loaded with a first therapeutic agent and the second group of therapeutic-agent-containing particles comprises second polymeric particles loaded with a second therapeutic agent. The first and second polymeric particles may be the same or different (i.e., they may have the same or different chemical composition), and the first and second therapeutic agents may be the same or different. Typically, at least one of (a) the first and second polymeric particles and (b) the first and second therapeutic agents is different.

For example, in some embodiments, the first and second polymeric particles are the same, whereas the first and second therapeutic agents are different. This may be advantageous, for instance, in that a manufacturer or healthcare provider can control the ratio of two (or more) differing therapeutic agents that are administered to the subject (e.g., by varying the ratio of the first and second groups of therapeutic-agent-containing particles).

In other embodiments, the first and second polymeric particles are different, whereas the first and second therapeutic agents are the same. This may be advantageous, for example, in that a manufacturer or health care provider can tailor the overall release profile of a given therapeutic agent. For example, the overall release profile can be tailored by varying the ratio of the first and second groups of particles, each of which can have a different release profile due to the difference in composition between the first and second polymeric particles (e.g., one group may be adapted for shorter term "burst" release and the other may be adapted for longer term "sustained" release).

In other embodiments, the first and second polymeric particles are different and the first and second therapeutic agents are different. This may be advantageous, for example, in that a manufacturer or health care provider can control the ratio of two (or more) therapeutic agents that are administered to the subject while at the same time providing the ability to tailor the release profile for each therapeutic agent (e.g., by pairing each therapeutic agent with a suitable polymeric particle).

In some embodiments, first and second groups of polymeric particles or first and second groups of therapeutic-agent-containing particles may be provided in an admixture. This may be advantageous, for example, in that a manufacturer can optimize the ratio of the first and second groups of particles that are delivered to the subject.

In some embodiments, a kit may be provided in which the first and second groups of therapeutic-agent-containing particles are provided separately (e.g., in separate containers). This may be advantageous, for example, in that a health care provider can select the ratio of the first and second groups of particles that are delivered to the subject.

In accordance with another aspect of the invention, first and second groups of injectable polymeric particles are provided, which differ from each other, which do not comprise a therapeutic agent, and which may either be provided in an admixture or provided separately (e.g., in a kit). This may be advantageous, for example, in that a health care provider can load the first and second groups of particles with one or more therapeutic agents of choice (which may be provided in a kit or independently provided) in a clinical setting, thereby providing the practitioner with the ability to tailor the type of therapeutic agent(s) delivered and the release profile(s) of the same.

The injectable particles may be used to treat various diseases and conditions in a variety of subjects. Subjects include vertebrate subjects, particularly humans and various warm-blooded animals, including pets and livestock. As used herein, "treatment" refers to the prevention of a disease or condition, the reduction or elimination of symptoms associated with a disease or condition, or the substantial or complete elimination of a disease or condition.

The injectable particles of the invention may vary in shape. In certain embodiments, they are substantially spherical, for example, having the form of a perfect (to the eye) sphere or the form of a near-perfect sphere such as a prolate spheroid (a slightly elongated sphere) or an oblate spheroid (a slightly flattened sphere), among other possibilities. In embodiments where the particles are substantially spherical, at least half of the particles (50% or more, for example, from 50% to 75% to 90% to 95% or more of a particle sample) may have a sphericity of 0.8 or more (e.g., from 0.80 to 0.85 to 0.9 to 0.95 to 0.97 or more). The sphericity of a collection of particles can be determined, for example, using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures the particles in an image. The sphericity of a particle, which is computed as $Da/Dp$ (where $Da=\sqrt{(4A/\pi)}$; $Dp=P/\pi$; A=pixel area; P=pixel perimeter), is a value from zero to one, with one representing a perfect circle.

The injectable particles of the invention can vary in size, with typical longest linear cross-sectional dimensions (e.g., for a sphere, the diameter) ranging, for example, from 100 to 150 to 250 to 500 to 750 to 1000 to 1500 to 2000 to 2500 to 5000 microns (µm).

For a collection of particles, the arithmetic mean maximum for the group typically ranges, for example, from 100 to 150 to 250 to 500 to 750 to 1000 to 1500 to 2000 to 2500 to 5000 microns (µm). The arithmetic mean maximum dimension of a group of particles can be determined using a Beckman Coulter RapidVUE Image Analyzer version 2.06 (Beckman Coulter, Miami, Fla.), described above. The arithmetic mean maximum dimension of a group of particles (e.g., in a composition) can be determined by dividing the sum of the maximum dimensions (e.g., the diameter, for a sphere) of all of the particles in the group by the number of particles in the group.

In some embodiments, at least 95 vol % of the particles within a group have a longest linear cross-sectional dimension between 40 µm and 5000 µm. For example, where the particles are spherical at least 95 vol % of the particles may have a diameter between 40 µm and 5000 µm.

As used herein a "porous particle" is a particle that contains pores, which may be observed, for example, by viewing the pores using a suitable microscopy technique such as scanning electron microscopy. Pore size may vary widely, ranging from 1 micron or less to 2 microns to 5 microns to 10 microns to 25 microns to 50 microns to 100 microns or more. Pores can come in a wide range of shapes. Pores may depend on the size of the particle.

As used herein a "polymeric particle" is one that contains polymers (also referred to herein as "particle-forming polymers"), for example, from 25 wt % or less to 50 wt % to 75 wt % to 90 wt % to 95 wt % to 97.5 wt % to 99 wt % or more polymers.

As used herein, "polymers" are molecules that contain multiple copies of one or more types of constitutional units, commonly referred to as monomers. The number of monomers/constitutional units within a given polymer may vary widely, ranging, for example, from 5 to 10 to 25 to 50 to 100 to 1000 to 10,000 or more constitutional units. As used herein, the term "monomers" may refer to free monomers and to those that are incorporated into polymers, with the distinction being clear from the context in which the term is used.

Polymers for use in the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains, such as graft polymers), dendritic architectures (e.g., arborescent and hyperbranched polymers), and networked architectures (e.g., crosslinked polymers), among others.

Polymers containing a single type of monomer are referred to herein as homopolymers, whereas polymers containing two or more types of monomers are referred to herein as copolymers. The two or more types of monomers within a given copolymer may be present in any of a variety of distributions including random, statistical, gradient and periodic (e.g., alternating) distributions, among others. One particular type of copolymer is a "block copolymer," which is a copolymer that contains two or more polymer blocks of different composition. As used herein, a "block" or "polymer block" is a grouping of constitutional units (e.g., 5 to 10 to 25 to 50 to 100 to 250 to 500 to 1000 or more units). Blocks can be unbranched or branched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As noted above, in some embodiments of the present invention, two or more groups of polymeric particles are provided which are different (i.e., they have a different chemical composition). For example, in some embodiments, a first group of polymeric particles may be formed using a polymer (also referred to herein as a "particle-forming polymer") that is not found in a second group of polymeric particles, a second group of polymeric particles may be formed using a polymer that is not found in a first group of polymeric particles, or both. As another example, in some embodiments, first and second groups of polymeric particles may be formed, after which a polymer within the first group, the second group, or both, is chemically modified.

Polymeric particles in accordance with the invention may be biostable or bioresorbable. As used herein, a polymeric particle is "bioresorbable" if it disintegrates in vivo due to one or more mechanisms such as dissolution, biodegradation, and so forth. On the other hand, a polymeric particle is "biostable" if it does not disintegrate in vivo.

As used herein, a polymer is "biodegradable" if it undergoes bond cleavage along the polymer backbone in vivo, regardless of the mechanism of bond cleavage (e.g., enzymatic breakdown, hydrolysis, oxidation, etc.).

In some embodiments of the invention, the polymeric particles are hydrogel particles. As used herein, a "hydrogel" is a crosslinked hydrophilic polymer (e.g., a polymer network) which swells when placed in water or biological fluids, but remains insoluble due to the presence of cross-links, which may be, for example, physical, chemical, or both. For instance, a hydrogel particle in accordance with the invention may undergo swelling in water such that its longest linear cross-sectional dimension (e.g., for a sphere, the diameter) increases by 5% or less to 10% to 15% to 20% to 25% or more. In some instances, the insolubility of the hydrogel is not permanent, and the particles are ultimately bioresorbed.

Specific polymers from which particles may be formed in accordance with the invention may be hydrophobic, hydrophilic or amphiphilic, they may be charged or uncharged, and they may be biostable or biodegradable. Specific polymers may be selected, for example, from one or more suitable members of the following, among others: polycarboxylic acid homopolymers and copolymers including polyacrylic acid, polymethacrylic acid, ethylene-methacrylic acid copolymers and ethylene-acrylic acid copolymers, where some of the acid groups can be neutralized with either zinc or sodium ions (commonly known as ionomers); acetal homopolymers and copolymers; acrylate and methacrylate homopolymers and copolymers (e.g., n-butyl methacrylate); cellulosic homopolymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene homopolymers and copolymers; polyimide homopolymers and copolymers such as polyether block imides, polyamidimides, polyesterimides, and polyetherimides; polysulfone homopolymers and copolymers including polyarylsulfones and polyethersulfones; polyamide homopolymers and copolymers including nylon 6,6, nylon 12, polycaprolactams, polyacrylamides and polyether block amides; resins including alkyd resins, phenolic resins, urea resins, melamine resins, epoxy resins, allyl resins and epoxide resins; polycarbonate homopolymers and copolymers; polyacrylonitrile homopolymers and copolymers; polyvinylpyrrolidone homopolymers and copolymers (cross-linked and otherwise); homopolymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-alkylene copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene (SIBS) block copolymers such as those disclosed in U.S. Pat. No. 6,545,097 to Pinchuk), poly[(styrene-co-p-methylstyrene)-b-isobutylene-b-(styrene-co-p-methylstyrene)] (SMIMS) triblock copolymers described in S. J. Taylor et al., *Polymer* 45 (2004) 4719-4730; polyphosphonate homopolymers and copolymers; polysulfonate homopolymers and copolymers, for example, sulfonated vinyl aromatic polymers and copolymers, including block copolymers having one or more sulfonated poly(vinyl aromatic) blocks and one or more polyalkene blocks, for example, sulfonated polystyrene-polyolefin-polystyrene triblock copolymers such as the sulfonated SEBS copolymers described in U.S. Pat. No. 5,840,387, and sulfonated versions of SIBS and SMIMS, which polymers may be sulfonated, for example, using the processes described in U.S. Pat. Nos. 5,840,387 and 5,468,574, among other sulfonated block copolymers; polyvinyl ketones, polyvinylcarbazoles, and polyvinyl esters such as polyvinyl acetates; polybenzimidazoles; polyalkyl oxide homopolymers and copolymers including polyethylene oxides (PEO); polyesters including polyethylene terephthalates and aliphatic polyesters such as homopolymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether homopolymers and copolymers including polyarylethers such as polyphenylene ethers, polyether ketones, polyether ether ketones; polyphenylene sulfides; polyisocyanates; polyolefin homopolymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated homopolymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone homopolymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylene polymers; polyiminocarbonates;

copoly(ether-esters) such as polyethylene oxide-polylactic acid copolymers; polyphosphazines; polyalkylene oxalates; polyoxaamides and polyoxaesters (including those containing amines and/or amido groups); polyorthoesters; polyamine and polyimine homopolymers and copolymers; biopolymers, for example, polypeptides including anionic polypeptides such as polyglutamate and cationic polypeptides such as polylysine, proteins, polysaccharides, and fatty acids (and esters thereof), including fibrin, fibrinogen, collagen, elastin, chitosan, gelatin, starch, glycosaminoglycans such as hyaluronic acid; as well as further copolymers, derivatives (e.g., esters, etc.) and mixtures of the foregoing.

Examples of hydrophilic particle-forming polymers for use in the present invention, not necessarily exclusive of those set forth above, may be selected from suitable homopolymers and copolymers of the following, among many others: acrylic acid, methacrylic acid, acrylamides including N-alkylacrylamides, alkylene oxides such as ethylene oxide and propylene oxide, vinyl alcohol, vinyl pyrrolidone, ethylene imine, ethylene amines, acrylonitrile, vinyl sulfonic acid, amino acids such as lysine and glutamic acid, maleic anhydride, hydrophilic polyurethanes, proteins, collagen, cellulosic polymers such as methyl cellulose and carboxymethyl cellulose, dextran, carboxymethyl dextran, modified dextran, alginic acid, pectinic acid, hyaluronic acid, chitin, pullulan, gelatin, gellan, xanthan, starch, carboxymethyl starch, chondroitin sulfate, guar, and derivatives and mixtures of the foregoing. Many of these polymers may be physically crosslinked, chemically crosslinked, or both, to form hydrogels.

Examples of biodegradable particle-forming polymers, not necessarily exclusive of those set forth above, may be selected from suitable members of the following, among many others: (a) polyester homopolymers and copolymers such as polyglycolic acid (PGA), polylactic acid (PLA) including poly-L-lactic acid, poly-D-lactic acid and poly-D, L-lactic acid, poly(beta-hydroxybutyrate), polygluconate including poly-D-gluconate, poly-L-gluconate, poly-D,L-gluconate, poly(epsilon-caprolactone), poly(delta-valerolactone), poly(p-dioxanone), poly(lactic acid-co-glycolic acid) (PLGA), poly(lactic acid-co-delta-valerolactone), poly(lactic acid-co-epsilon-caprolactone), poly(lactic acid-co-beta-malic acid), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) poly(ortho esters) such as those synthesized by copolymerization of various diketene acetals and diols, among others, (c) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis (p-carboxyphenoxy)hexane anhydride], among others; (d) polycarbonate homopolymers and copolymers such as poly (trimethylene carbonate), poly(lactic acid-co-trimethylene carbonate) and poly(glycolic acid-co-trimethylene carbonate), among others, and (e) amino-acid-based polymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyesteramides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

Polymers may be selected, for instance, based on their ability to interact with therapeutic agents in a general or specific fashion, for example, based on non-covalent interactions such as van der Waals forces, hydrophobic interactions and/or electrostatic interactions (e.g., charge-charge interactions, charge-dipole interactions, and dipole-dipole interactions, including hydrogen bonding). Examples of specific non-covalent interactions include π-π stacking, binding based on the formation of multiple hydrogen bonds, binding based on the formation of complexes and/or coordinative bonds (e.g., metal ion chelation, etc.), binding based on antibody-antigen interactions, also sometimes referred to as antibody-hapten interactions, protein-small molecule interactions (e.g., avidin/streptavidin-biotin binding), protein-protein interactions, and so forth. Specific chemical entities may be covalently attached to the particle-forming polymers for this purpose, either during synthesis or post-synthesis.

As one example, particles may contain one or more groups that electrostatically interact with (e.g., via ion exchange, complexation, coordination, chelation, etc.) a charged therapeutic agent (e.g., a charged radioisotope for radio-embolization therapy, a charged small molecule drug such as a charged anti-neoplastic agent, etc.).

A benefit of this approach, as it pertains to radioisotopes, is that the particles need not be exposed to high energy radiation associated with the conversion of non-radioactive isotopes (e.g., $^{89}Y$) to radioactive isotopes (e.g., $^{90}Y$). Instead, the particles can be loaded with the charged therapeutic agent after it is exposed to the high energy radiation. In this regard, the exposure of many polymers to the levels of radiation needed to convert non-radioactive isotopes to radioactive ones would result in significant changes to the polymers (e.g., extensive chain scission and or crosslinking) which would dramatically alter the chemical and/or mechanical properties of the particles.

Among other characteristics, the therapeutic agents may be, for example, hydrophobic, hydrophilic or amphiphilic, and they may be negatively charged, positively charged, zwitterionc, or of neutral charge.

Examples of therapeutic agents for use in the particles of the present invention include anti-thrombotic/anti-clotting/anti-coagulant agents (e.g., heparin, heparin derivatives, urokinase, dextrophenylalanine proline arginine chloromethylketone (PPack), an RGD peptide-containing compound, heparin, hirudin, anti-thrombin compounds including anti-thrombin antibodies, platelet receptor antagonists, anti-platelet receptor antibodies, aspirin, prostaglandin inhibitors, platelet inhibitors and tick antiplatelet factors or peptides); thrombogenic agents and agents that promote clotting; antioxidants; angiogenic agents, anti-angiogenic agents; anti-proliferative agents; calcium entry blockers (e.g., verapamil, diltiazem, nifedipine); survival genes which protect against cell death (e.g., anti-apoptotic Bcl-2 family factors and Akt kinase); steroidal and non-steroidal anti-inflammatory agents (e.g., dexamethasone, prednisolone, corticosterone, budesonide, estrogen, acetyl salicylic acid, sulfasalazine, mesalamine, etc.); anesthetic agents (e.g., lidocaine, bupivacaine and ropivacaine); protein kinase and tyrosine kinase inhibitors; cytostatic agents (i.e., agents that prevent or delay cell division in proliferating cells, for example, by inhibiting replication of DNA or by inhibiting spindle fiber formation) (e.g., toxins, methotrexate, adriamycin, radionuclides, protein kinase inhibitors such as staurosporin and diindoloalkaloids, etc.), agents that inhibit intracellular increase in cell volume (i.e., the tissue volume occupied by a cell) such as cytoskeletal inhibitors (e.g., colchicine, vinblastin, cytochalasins, paclitaxel, etc.) or metabolic inhibitors (e.g., staurosporin, Pseudomonas exotoxin, modified diphtheria and ricin toxins, etc.); trichothecenes (e.g., a verrucarin or roridins); agents acting as an inhibitor that blocks cellular protein synthesis and/or secretion or organization of extracellular matrix (i.e., an "anti-matrix agent" such as colchicine or tamoxifen); various pharmaceutically acceptable salts and derivatives of the foregoing, and combinations of the foregoing, among other agents.

Examples of therapeutic agents which may be used in the particles of the invention thus include toxins (e.g., ricin toxin, radioisotopes, etc.) and other agents able to kill undesirable cells (e.g., those making up cancers and other tumors such as uterine fibroids) or to slow or arrest growth of undesirable cells, among other agents.

Further specific examples of therapeutic agents for use in the particles of the invention, not necessarily exclusive of those above, may be selected from suitable members of the following: radioisotopes (e.g., $^{90}$Y, $^{32}$P, $^{18}$F, $^{140}$La, $^{153}$Sm, $^{165}$Dy, $^{166}$Ho, $^{169}$Er, $^{169}$Yb, $^{177}$Lu, $^{186}$Re, $^{188}$Re, $^{103}$Pd, $^{198}$Au, $^{192}$Ir, $^{90}$Sr, $^{111}$In or $^{67}$Ga), which may be covalently bound or non-covalently bound to another species, antineoplastic/antiproliferative/anti-mitotic agents including antimetabolites such as folic acid analogs/antagonists (e.g., methotrexate, etc.), purine analogs (e.g., 6-mercaptopurine, thioguanine, cladribine, which is a chlorinated purine nucleoside analog, etc.) and pyrimidine analogs (e.g., cytarabine, fluorouracil, etc.), alkaloids including taxanes (e.g., paclitaxel, docetaxel, etc.), alkylating agents such as alkyl sulfonates, nitrogen mustards (e.g., cyclophosphamide, ifosfamide, etc.), nitrosoureas, ethylenimines and methylmelamines, other aklyating agents (e.g., dacarbazine, etc.), antibiotics and analogs (e.g., daunorubicin, doxorubicin, idarubicin, mitomycin, bleomycins, plicamycin, etc.), antiestrogens (e.g., tamoxifen), antianidrogens (e.g., flutamide), platinum complexes (e.g., cisplatin, carboplatin, etc.), antineoplastic enzymes (e.g., asparaginase, etc.), agents affecting microtubule dynamics (e.g., vinblastine, vincristine, colchicine, Epo D, epothilone), caspase activators, proteasome inhibitors, angiogenesis inhibitors (e.g., statins such as endostatin, cerivastatin and angiostatin, squalamine, etc.), olimus family drugs (e.g., sirolimus, everolimus, tacrolimus, zotarolimus, etc.), etoposides, as well as many others (e.g., hydroxyurea, flavopiridol, procarbizine, mitoxantrone, campothecin, etc.), various pharmaceutically acceptable salts and derivatives (e.g., esters, etc.) of the foregoing, and combinations of the foregoing, among other agents.

Further therapeutic agents include chemical ablation agents (materials whose inclusion in the formulations of the present invention in effective amounts results in necrosis or shrinkage of nearby tissue upon injection) including osmotic-stress-generating agents (e.g., salts, etc.), basic agents (e.g., sodium hydroxide, potassium hydroxide, etc.), acidic agents (e.g., acetic acid, formic acid, etc.), enzymes (e.g., collagenase, hyaluronidase, pronase, papain, etc.), free-radical generating agents (e.g., hydrogen peroxide, potassium peroxide, etc.), other oxidizing agents (e.g., sodium hypochlorite, etc.), tissue fixing agents (e.g., formaldehyde, acetaldehyde, glutaraldehyde, etc.), coagulants (e.g., gengpin, etc.), non-steroidal anti-inflammatory drugs, contraceptives (e.g., desogestrel, ethinyl estradiol, ethynodiol, ethynodiol diacetate, gestodene, lynestrenol, levonorgestrel, mestranol, medroxyprogesterone, norethinidrone, norethynodrel, norgestimate, norgestrel, etc.), GnRH agonists (e.g., buserelin, cetorelix, decapeptyl, deslorelin, dioxalan derivatives, culexin, ganirelix, gonadorelin hydrochloride, goserelin, goserelin acetate, histrelin, histrelin acetate, leuprolide, leuprolide acetate, leuprorelin, lutrelin, nafarelin, meterelin, triptorelin, etc.), antiprogestogens (e.g., mifepristone, etc.), selective progesterone receptor modulators (SPRMs) (e.g., asoprisnil, etc.), various pharmaceutically acceptable salts and derivatives of the foregoing, and combinations of the foregoing, among other agents.

For tissue bulking applications (e.g., urethral bulking, cosmetic bulking, etc.), specific beneficial therapeutic agents include those that promote collagen production, including proinflammatory agents and sclerosing agents such as those listed Pub. No. US 2006/0251697.

Suitable proinflammatory agents can be selected, for example, from suitable endotoxins, cytokines, chemokines, prostaglandins, lipid mediators, and other mitogens. Specific examples of known proinflammatory agents from which suitable proinflammatory agents can be selected include the following: growth factors such as platelet derived growth factor (PDGF), fibroblast growth factor (FGF), transforming growth factor (such as TGF-alpha and TGF-beta), epidermal growth factor (EGF), insulinlike growth factor (IGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), superoxide, hydrogen peroxide, zymosan, bacterial lipopolysaccharide, imiquimod, various pharmaceutically acceptable salts and derivates of the foregoing, and combinations of the foregoing, among other agents.

Suitable sclerosing agents for the practice of the invention can be selected, for example, from the following (which list is not necessarily exclusive of the agents set forth above): inorganic materials such as aluminum hydroxide, sodium hydroxide, silver nitrate and sodium chloride, as well as organic compounds, including alcohols such as ethanol, acetic acid, trifluoroacetic acid, formaldehyde, dextrose, polyethylene glycol-ethers (e.g., polidocanol, also known as laureth 9, polyethylene glycol (9) monododecyl ether, and hydroxypolyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyanoactyalte and methyl 2-cyanoacrylate, ethanolamine, ethanolamine oleate, bacterial preparations (e.g., corynebacterium and streptococcal preparations such as picibanil) and mixtures of the same, among others.

In certain embodiments, the particles of the invention may include one or more radiopaque materials, materials that are visible under magnetic resonance imaging (MRI-visible materials), ferromagnetic materials, and/or ultrasound contrast agents. These materials can, for example, be covalently bonded to non-covalently associated with the particles. Various radiopaque materials, MRI-visible materials, ferromagnetic materials, and contrast agents are described, for example, in Pub. No. US 2004/0101564 A1 to Rioux et al.

Polymeric particles for use in the invention may be formed by any suitable particle forming method, including emulsion/solvent evaporation methods, precipitation methods, and droplet solidification methods, among many others.

The following discussion pertains to the formation of polymeric particles from polyols such as polyvinyl alcohol (PVA) for purposes of further illustrating the invention, but the invention is clearly not so-limited.

The monomer of PVA (vinyl alcohol), does not exist in a stable free form, due to keto-enol rearrangement with its tautomer (acetaldehyde). Typically, PVA is produced by the polymerization of a vinyl ester, such as vinyl acetate, to form a polyvinyl ester such as polyvinyl acetate (PVAc). Then the polyvinyl ester is subjected to hydrolysis to convert the ester groups to hydroxyl groups. The hydrolysis reaction, however, does not typically go to completion, resulting in polymers with a certain degree of hydrolysis that depends on the extent of reaction. Thus, PVA is generally a copolymer of vinyl alcohol monomers,

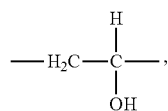

and vinyl ester monomers, typically, vinyl acetate monomers,

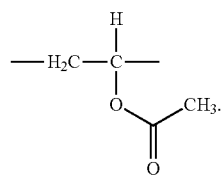

Commercial PVA grades are available with varying degrees of hydrolysis (e.g., 50% to 99% or more) including grades with high degrees of hydrolysis (above 98.5%). The degree of hydrolysis (or, conversely, the ester group content) of the polymer has an effect on its chemical properties, crystallizability, and solubility, among other properties. For example, degrees of hydrolysis and polymerization are known to affect the solubility of PVA in water, with PVA grades having high degrees of hydrolysis being known to have reduced solubility in water relative to those having low degrees of hydrolysis. For further information on PVA (as well as PVA hydrogels), see, e.g., C. M. Hassan et al., "Structure and Applications of Poly(vinyl alcohol) Hydrogels Produced by Conventional Crosslinking or by Freezing/Thawing Methods," *Adv. Polym. Sci.*, 153, 37-65 (2000) and N. A. Peppas et al., "Hydrogels in Biology and Medicine: From Fundamentals to Bionanotechnology", *Adv. Mater.*, 18, 1345-1360 (2006).

As noted above, hydrogels are crosslinked hydrophilic polymers (e.g., polymer networks) which swell when placed in water or biological fluids, but remain insoluble due to the presence of crosslinks, which may be, for example, physical, chemical, or a combination of both.

Polyols such as PVA can be crosslinked, for example, through the use of chemical crosslinking agents. Some of the common chemical crosslinking agents that have been used for polyol hydrogel preparation include glutaraldehyde, acetaldehyde, formaldehyde, and other monoaldehydes. In the presence of an acid (e.g., sulfuric acid, acetic acid, etc.) these crosslinking agents form acetal bridges between the pendant hydroxyl groups found on the polyol chains. For example, acetal formation may link two alcohol moieties together according to the following scheme:

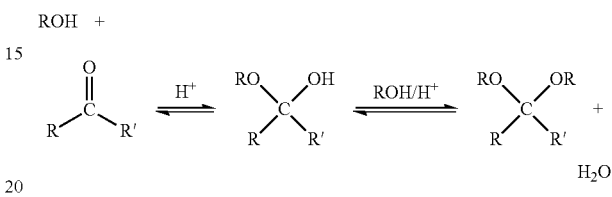

where R and R' are organic groups. For species with multiple hydroxyl groups, including polyols such as PVA, two hydroxyl groups within the same molecule may react according to the following scheme:

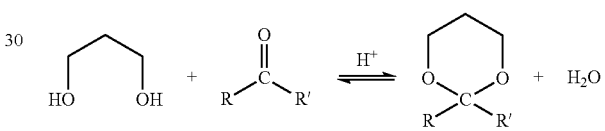

As noted in Pub. No. US 2003/0185895 to Lanphere et al., in certain instances, the reaction of PVA with an aldehyde (formaldehyde) in the presence of an acid is primarily a 1,3 acetalization:

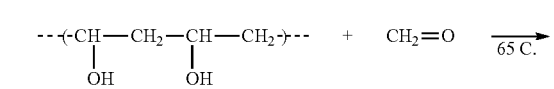

Such intra-chain acetalization reaction can be carried out with relatively low probability of inter-chain crosslinking. Since the reaction proceeds in a random fashion, there will be leftover —OH groups that do not react with adjacent groups. Moreover, the residual vinyl ester groups do not take part in the above reactions. Thus, PVA crosslinked in this fashion can be considered a copolymer of the following monomers: vinyl alcohol monomers,

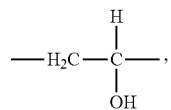

vinyl ester monomers, typically vinyl acetate monomers

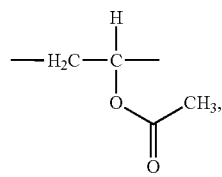

and vinyl formal monomers of the following structure,

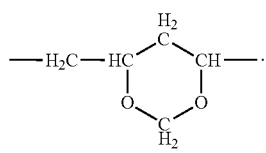

Examples of ranges for each of these monomer units are as follows, among others: 5-20 mole % vinyl alcohol monomer units, 0 to 20 mole % vinyl acetate monomer units, and 40 to 90 mole % vinyl formal monomer units. The weight percent of a monomer unit in a polymer can be measured using solid-state NMR spectroscopy.

Other mechanisms of hydrogel preparation involve physical crosslinking due to crystallite formation (e.g., due to freeze-thaw processing) and chemical crosslinking using ionizing radiation such as electron-beam and gamma-ray irradiation. These methods may in some instances be advantageous over techniques that employ chemical cross-linking agents, because they do not leave behind non-reacted chemical species.

As a specific example, porous polyol spheres may be formed as described in Pub. No. US 2003/0185895 to Lanphere et al. Briefly, a solution containing a polyol such as PVA and a gelling precursor such as sodium alginate may be delivered to a viscosity controller, which heats the solution to reduce its viscosity prior to delivery to a droplet generator. The droplet generator forms and directs drops into a gelling solution containing a gelling agent which interacts with the gelling precursor. For example, in the case where an alginate gelling precursor is employed, an agent containing a divalent metal cation such as calcium chloride may be used as a gelling agent, which stabilizes the drops by gel formation based on ionic crosslinking. The concentration of the gelling agent can control void formation in the particle, thereby controlling the porosity gradient in the particle. Adding non-gelling ions, for example, sodium ions, to the gelling solution can limit the porosity gradient, resulting in a more uniform intermediate porosity throughout the particle. The gel-stabilized drops may then be transferred to a reactor vessel where tie polymer in the gel-stabilized drops reacted, thereby forming precursor particles. For example, the reactor vessel may include an agent that chemically reacts with the polyol to cause interchain or intrachain crosslinking. For instance, the vessel may include an aldehyde and an acid, leading to acetalization of the polyol. The precursor particles are then transferred to a gel dissolution chamber, where the gel is dissolved. For example, ionically crosslinked alginate may be removed by ion exchange with a solution of sodium hexa-metaphosphate. Alginate may also be removed by radiation degradation. Porosity is generated due to the presence (and ultimate removal) of the alginate. The particles may then be filtered to remove any residual debris and to sort the particles into desired size ranges.

Using the above and other techniques, porous particles may be formed having a variety of pore sizes and porosities. Moreover, porous acetalized PVA particles are commercially available (e.g., as Contour SE™ embolic agent, Boston Scientific, Natick, Mass., USA).

In some embodiments of the invention, charged species (e.g., those that are charged at neutral pH in aqueous solution) may be covalently bound to particle-forming polymers within the particles of the invention. Examples of such charged species include monomers such as styrene sulfonic acid, acrylic acid, vinyl amine, vinyl pyridine, or dimethylaminoethyl acrylate, and polymers such as poly(styrene sulfonic acid), poly(acrylic acid), poly(vinyl amine), poly(vinyl pyridine) or poly(dimethylaminoethyl acrylate). The chemical species can be covalently bound to the particle-forming polymers using any desired method. For example, in some embodiments, the charged species are introduced during the polymer formation process. For example, particle-forming polymers may be formed using charged monomers, or precursors thereof. In other embodiments, the charged species are introduced after the polymer formation process but before the particle formation process (e.g., by post-synthesis modification of the polymers, for instance, via sulfonation, or via another reaction, such as the covalent bonding reactions described below). In still other embodiments, the charged species are introduced after the particle formation process, for example, by bringing the chemical species to be covalently bonded into contact with the particles. This may be achieved, for example, by coating the particles with, or soaking the particles in, a solution of the chemical species. In certain embodiments, the chemical species are diffused into the pores of the particle. Subsequently, the chemical species are covalently bonded to the polymers within the particles.

For example, the chemical species and particle-forming polymers can be covalently bound by exposure to a suitable type of radiation (e.g., electron beam radiation, gamma radiation, UV radiation, etc.). As one specific example, gamma radiation or an electron beam can be used to covalently bond monomeric or polymeric styrene sulfonic acid, acrylic acid, vinyl amine, vinyl pyrrolidone, or dimethylaminoethylacrylate to formalized or unformalized PVA. Exposure to radiation may crosslink the particle-forming polymers in some embodiments, in which case it may be desirable to covalently bond the species to the particle-forming polymers after particle formation has occurred. Alternatively (or in addition) a chemical species can be covalently bound to a particle-forming polymer by reaction between a polymerization initiator incorporated into the polymer and one or more types of monomers exposed to such a polymer.

Once suitable polymeric particles are obtained, in accordance with an aspect of the invention, the particles may be loaded with a therapeutic agent. In one method, polymeric particles are exposed to a solution containing one or more therapeutic agents. To increase solution uptake, the polymeric particles may be dried by any suitable method, including lyophilization (freeze drying). Using dry particles, solution uptake is enhanced, much like a dry sponge is able to absorb more liquid than a wet sponge. Depending on the nature of the polymeric particles and the therapeutic agents, the solvent systems used to create the solution may be based on (a) water, (b) one or more organic solvents, or (c) water and one or more organic solvents. Typically, the one or more therapeutic agents should be soluble in the selected solvent system. Furthermore, the selected solvent system should not destroy the integrity of the polymeric particles.

In some embodiments, a solvent system is selected that swells the particles to some degree. In those specific embodiments where the polymeric particles are hydrogels, the solvent system may be, for example, based upon water, upon one or more polar organic solvents (e.g., ethanol, methanol, acetone, dimethylsulfoxide (DMSO), dimethylformamide (DMF), etc.), or upon water plus one or more polar organic solvents. Polar organic solvents may be used, for example, in conjunction with the loading of more hydrophobic therapeutic agents.

As noted above, in various embodiments, polymeric particles for use in the invention may contain charged groups, for example, cationic groups (e.g., ammonio groups, iminio groups, etc.), anionic groups (e.g., carboxylate groups, phosphate groups, sulfonate groups, etc.), or both. Such particles may be paired with charged therapeutic agents to take advantage of electrostatic interactions. For example, particles having cationic groups may be paired with negatively charged therapeutic agents, or particles having anionic groups may be paired with positively charged therapeutic agents.

For instance, in some embodiments acidic particles (e.g., ones having acidic groups such as —COOH groups, —SO$_3$H groups, —PO(OH)$_2$ groups, etc.) may be admixed with a basic therapeutic agent (e.g., one having one or more basic groups, for instance, —NH$_2$ groups, =NH groups, etc.) for loading of the same. In other embodiments, basic particles may be admixed with an acidic therapeutic agents. In either case, acid-base neutralization may yield particles and agents of opposite charge, resulting in electrostatic interactions.

In other embodiments, salt forms of oppositely charged therapeutic agents and particles are mixed. For example, particles having negatively charged groups (e.g., —COO$^-$ groups, —SO$_3^-$ groups, —PO(OH)O$^-$ groups, etc.) may be admixed with a positively charged therapeutic agents (e.g., those having —NH$_3^+$ groups, =NH$_2^+$ groups, etc.), or particles having positively charged groups may be admixed with negatively charged therapeutic agents. Salt forms for positively charged particles/agents include those based on inorganic and organic acids (including amino acids, hydroxyacids and fatty acids), for instance, hydrochloride, hydrobromide, sulfate, nitrate, phosphate, mesylate, tosylate, acetate, propionate, maleate, benzoate, salicylate, fumarate, glutamate, aspartate, citrate, lactate, succinate, tartrate, hexanoate, octanoate, decanoate, oleate and stearate salt forms, among others. Salt forms for negatively charged particles/agents include those based on metals and amines (including amino acids), for instance, sodium, potassium, calcium, magnesium, zinc, triethylamine, ethanolamine, triethanolamine, meglumine, ethylene diamine, choline, arginine, lysine and histidine salt forms, among others.

The amount of therapeutic agent within the injectable particles of the present invention will vary widely depending on a number of factors, including the disease, disorder or condition being treated, the potency of the therapeutic agent, and the volume of injectable particles ultimately injected into the subject, among other factors. Typical therapeutic agent concentration ranges are, for example, from about 0.1 or less to 0.2 to 0.5 to 1 to 2 to 5 to 10 to 20 to 50 wt % or more of the therapeutic-agent-containing particles, among other possibilities.

As noted above, in accordance with one aspect of the invention, first and second groups of therapeutic-agent-containing particles are provided, in which the first group of therapeutic-agent-containing particles contains first polymeric particles loaded with a first therapeutic agent and the second group of therapeutic-agent-containing particles contains second polymeric particles loaded with a second therapeutic agent. If desired, additional therapeutic-agent-containing particles may be provided (for example, a third group of therapeutic-agent-containing particles containing third polymeric particles loaded with a third therapeutic agent, and so forth).

In some embodiments, the first and second polymeric particles are different and the first and second therapeutic agents are the same. Such embodiments are desirable, for instance, in complex release profiles can be created for a given therapeutic agent. For example, the first group of therapeutic-agent-containing particles can provide a release profile that is different from (e.g., faster than) the release profile of the second group of therapeutic-agent-containing particles. For example, after a period selected from 1 hour, 3 hours, 8 hours, 12 hours, 1 day, 3 days, 1 week, 2 weeks, 1 month, 2 months or 6 months, the percentage of therapeutic agent released by the first group of particles (i.e., the percentage of agent released relative to that loaded) in aqueous solution (e.g., in water, saline, PBS, etc.) may be at least 1.5 times greater than the percentage of therapeutic agent released by the second group of particles, for example ranging from 1.5 to 2 to 5 to 10 to 20 to 50 to 100 or more times the percentage of therapeutic agent released by the second group of particles. Moreover, the release profile can be further tailored by providing the first and second groups of therapeutic-agent-containing particles in various weight ratios, for example, ranging from 1:100 or less to 1:50 to 1:20 to 1:10 to 1:5 to 1:2 to 1:1 to 2:1 to 5:1 to 10:1 to 20:1 to 50:1 to 100:1 or more.

As an example, where the therapeutic-agent-containing particles are embolic particles, therapeutic agent may be selected from a pain-killing agent (e.g., an opoid, steroidal anti-inflammatory agent, nonsteroidal anti-inflammatory agent, etc.) or an agent that kills or shrinks tissue or that slows or stops tissue growth (e.g., a toxin, antineoplastic agent, ablation agent, etc.). As another example, where the therapeutic-agent-containing particles are tissue bulking particles, the particles may release an agent that promotes collagen production (e.g., a proinflammatory agent, a sclerosing agent, etc.) or a pain-killing agent.

In some embodiments, the first and second polymeric particles may be the same or different, whereas the first and second therapeutic agents are different. Such embodiments are desirable, for instance, in that the ratio of the first and second therapeutic agents can be controlled by the manufacturer or, where the particles are provided separately, by the health care provider (e.g., by controlling/taking into account the % load of each agent within the polymeric particles and by controlling the ratio of the first group of particles relative to the second group of particles, etc.). Moreover, by using different first and second polymeric particles, the release profiles of the first and second therapeutic agents can be independently controlled.

As a specific example, where the particles are embolic particles, the first group of therapeutic-agent-containing particles may release an agent that slows or stops tissue growth, or kills (necroses) or shrinks tissue, whereas the second group of therapeutic-agent-containing particles may release a pain-killing agent. As another specific example, where the particles a tissue bunking particles, the first group of therapeutic-agent-containing particles may release an agent that promotes collagen production, whereas the second group of therapeutic-agent-containing particles may release a pain-killing agent. In some of these embodiments, it may be desirable to release the pain-killing agent more rapidly that the other agent.

For a given polymeric particle and agent, release of the therapeutic agent may be slowed, for example, by crosslinking the particles after loading the particles with the therapeutic agent (e.g., by subjecting the particles to a chemical crosslinking agent or to ionizing radiation such as gamma rays, X rays, electron beams, etc.). Release may also be slowed, for example, by selecting a polymeric particle that has a hydrophobicity/hydrophilicity that matches that of the therapeutic agent or that modulates the permeation of biological fluids into the particles. Release may also be slowed, for example, by selecting a polymeric particle that promotes relatively strong non-covalent binding with the therapeutic agent (e.g., by providing the polymeric particles with particle-forming polymers having functional groups that promote electrostatic interactions such as charge-charge interactions, charge-dipole interactions, and dipole-dipole interactions, including hydrogen bonding). For example, a charged therapeutic agent may be paired with polymeric particles that contain functional groups of opposite charge, as described above.

The particles of the invention may be stored and transported in separate containers or in admixture. The particles of the invention may be stored and transported in dry form or in wet form (e.g., as an aqueous suspension). The particles of the invention may optionally contain additional agents such as one or more of the following among others: (a) tonicity adjusting agents including sugars (e.g., dextrose, lactose, etc.), polyhydric alcohols (e.g., glycerol, propylene glycol, mannitol, sorbitol, etc.) and inorganic salts (e.g., potassium chloride, sodium chloride, etc.), (b) suspension agents including various surfactants, wetting agents, and polymers (e.g., albumen, PEO, polyvinyl alcohol, block copolymers, etc.), (c) imaging contrast agents (e.g., Omnipaque™, Visipaque™, etc.), and (d) pH adjusting agents including various buffer solutes. Dry or wet compositions may be shipped, for example, in a syringe, catheter, vial, ampoule, or other container. Dry forms may be mixed with an appropriate liquid carrier (e.g. sterile water for injection, physiological saline, phosphate buffer, a solution containing an imaging contrast agent, etc.) prior to administration. In this way the concentration of the composition to be injected may be varied at will, depending on the specific application at hand, as desired by the healthcare practitioner in charge of the procedure. Wet forms (e.g., aqueous suspensions) may also be mixed with a suitable liquid carrier (e.g. sterile water for injection, physiological saline, phosphate buffer, a solution containing contrast agent, etc.) prior to administration, allowing the concentration of administered particles (as well as other optional agents) in the suspension to be reduced prior to injection, if so desired by the healthcare practitioner in charge of the procedure. One or more containers of liquid carrier may also be supplied and shipped, along with the dry or wet particles, in the form of a kit.

The amount of injectable particles within a suspension to be injected may be determined by those of ordinary skill in the art. The amount of particles may be limited by the fact that when the amount of particles in the composition is too low, too much liquid may be injected, possibly allowing particles to stray far from the site of injection, which may result in undesired embolization or bulking of vital organs and tissues. When the amount of particles is too great, the delivery device (e.g., catheter, syringe, etc.) may become clogged.

In certain embodiments, tie density of the liquid (e.g. aqueous phase) that suspends the particles is close to that of the particles themselves, thereby promoting an even suspension. The density of the aqueous phase may be increased, for example, by increasing the amount of solutes that are dissolved in the aqueous phase, and vice versa.

An "effective amount" of any of the particles of the invention is, for example, (a) an amount sufficient to produce an occlusion or emboli at a desired site in the body, (b) an amount sufficient to achieve the degree of bulking desired (e.g., an amount sufficient to improve urinary incontinence, vesicourethral reflux, fecal incontinence, ISD or gastroesophageal reflux, or an amount sufficient for aesthetic improvement), or (c) an amount sufficient to locally treat a disease, disorder or condition. Effective doses may also be extrapolated from dose-response curves derived from animal model test systems, among other techniques.

As noted above, permanent or temporary occlusion of blood vessels is useful for managing various diseases, disorders and conditions. Compositions including particles in accordance with the invention can thus be delivered to various sites in the body, including, for example, sites having tumors, such as those of the breast, prostate, lung, thyroid, or ovaries. The compositions can be used, for example, in neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, as fillers for AAA sacs (Type II endoleaks), as endoleak sealants, as arterial sealants, as puncture sealants, and can be used to provide occlusion of other lumens such as fallopian tubes. Internal bleeding includes gastrointestinal, urinary, renal and varicose bleeding, among other forms of bleeding. AVMs are, for example, abnormal collections of blood vessels (e.g. in the brain) which shunt blood from a high pressure artery to a low pressure vein, resulting in hypoxia and malnutrition of those regions from which the blood is diverted. In some embodiments, a composition containing tie particles can be used to prophylactically treat a condition.

Fibroids, also known as leiomyoma, leiomyomata or fibromyoma, are the most common benign tumors of the uterus. These non-cancerous growths are present in significant fraction of women over the age of 35. In most cases, multiple fibroids are present, often up to 50 or more. Fibroids can grow, for example, within the uterine wall ("intramural" type), on the outside of the uterus ("subserosal" type), inside the uterine cavity ("submucosal" type), between the layers of broad ligament supporting the uterus ("interligamentous" type), attached to another organ ("parasitic" type), or on a mushroom-like stalk ("pedunculated" type). Fibroids may range widely in size, for example, from a few millimeters to 40 centimeters. In some women, fibroids can become enlarged and cause excessive bleeding and pain. While fibroids have been treated in the past by surgical removal of the fibroids (myomectomy) or by removal of the uterus (hysterectomy), recent advances in uterine embolization now offer a nonsurgical treatment. Thus, injectable particles in accordance with the present invention can be used to treat uterine fibroids.

Methods for treatment of fibroids by embolization are well known to those skilled in the art (see, e.g., Pub. No. US 2003/0206864 to Mangin and the references cited therein). Uterine embolization is aimed at starving fibroids of nutrients. Numerous branches of the uterine artery may supply uterine fibroids. In the treatment of fibroids, embolization of the entire uterine arterial distribution network is often preferred. This is because it is difficult to selectively catheterize individual vessels supplying only fibroids, the major reason being that there are too many branches for catheterization and embolization to be performed in an efficient and timely manner. Also, it is difficult to tell whether any one vessel supplies fibroids rather than normal myometrium. In many women, the fibroids of the uterus are diffuse, and embolization of the entire uterine arterial distribution affords a global treatment for every fibroid in the uterus.

In a typical procedure, a catheter is inserted near the uterine artery by the physician (e.g., with the assistance of a guide wire). Once the catheter is in place, the guide wire is removed and contrast agent is injected into the uterine artery. The patient is then subjected to fluoroscopy or X-rays. In order to create an occlusion, an embolic agent is introduced into the uterine artery via catheter. The embolic agent is carried by the blood flow in the uterine artery to the vessels that supply the fibroid. The particles flow into these vessels and clog them, thus disrupting the blood supply to the fibroid. In order for the physician to view and follow the occlusion process, contrast agent may be injected subsequent to infusion of the embolic agent. Treatment is enhanced in the present invention by the therapeutic agent(s) that is/are present in the particles.

Controlled, selective obliteration of the blood supply to tumors is also used in treating solid tumors such as renal carcinoma, bone tumor and liver cancer, among various others. The idea behind this treatment is that preferential blood flow toward a tumor will carry the embolization agent to the tumor thereby blocking the flow of blood which supplies nutrients to the tumor, thus, causing it to shrink. Embolization may be conducted as an enhancement to chemotherapy or radiation therapy. As elsewhere herein, treatment is enhanced in the present invention by the therapeutic agent(s) that is/are present in the particles.

Particles in accordance with the invention may also be used to treat various other diseases, conditions and disorders, including treatment of the following: arteriovenous fistulas and malformations including, for example, aneurysms such as neurovascular and aortic aneurysms, pulmonary artery pseudoaneurysms, intracerebral arteriovenous fistula, cavernous sinus dural arteriovenous fistula and arterioportal fistula, chronic venous insufficiency, varicocele, pelvic congestion syndrome, gastrointestinal bleeding, renal bleeding, urinary bleeding, varicose bleeding, uterine hemorrhage, and severe bleeding from the nose (epistaxis), as well as preoperative embolization (to reduce the amount of bleeding during a surgical procedure) and occlusion of saphenous vein side branches in a saphenous bypass graft procedure, among other uses. As elsewhere herein, treatment is enhanced in the present invention by the therapeutic agent that is present in the particles.

Particles in accordance with the invention may also be used in tissue bulking applications, for example, as augmentative materials in the treatment of urinary incontinence, vesicourethral reflux, fecal incontinence, intrinsic sphincter deficiency (ISD) or gastro-esophageal reflux disease, or as augmentative materials for aesthetic improvement. For instance, a common method for treating patients with urinary incontinence is via periurethral or transperineal injection of a bulking material. In this regard, methods of injecting bulking agents commonly require the placement of a needle at a treatment region, for example, periurethrally or transperineally. The bulking agent is injected into a plurality of locations, assisted by visual aids, causing the urethral lining to coapt. In some cases, additional applications of hulking agent may be required. Treatment is enhanced in the present invention by the therapeutic agent (e.g., proinflammatory agents, sclerosing agents, etc.) that is present in the particles.

The present invention encompasses various ways of administering the particulate compositions of the invention to effect embolization, bulking or other procedure benefiting from therapeutic agent release. One skilled in the art can determine the most desirable way of administering the particles depending on the type of treatment and the condition of the patient, among other factors. Methods of administration include, for example, percutaneous techniques as well as other effective routes of administration. For example, the particulate compositions of the invention may be delivered through a syringe or through a catheter, for instance, a FasTracker® microcatheter (Boston Scientific, Natick, Mass., USA), which can be advanced over a guidewire, a steerable microcatheter, or a flow-directed microcatheter (MAGIC; Balt, Montomorency, France).

Various aspects of the invention of the invention relating to the above are enumerated in the following paragraphs:

Aspect 1. Injectable particles comprising (a) a first group of injectable particles comprising first polymeric particles loaded with a first therapeutic agent and (b) a second group of injectable particles comprising second polymeric particles loaded with a second therapeutic agent, wherein (i) the first and second polymeric particles are the same and the first and second therapeutic agents are different or (ii) the first and second polymeric particles are different and die first and second therapeutic agents are the same or (iii) wherein the first and second polymeric particles are different and the first and second therapeutic agents are different.

Aspect 2. The injectable particles of aspect 1, wherein 95 vol % of the first and second groups of polymeric particles have a longest linear cross-sectional dimension between 40 µm and 5000 µm.

Aspect 3. The injectable particles of aspect 1, wherein the first and second groups of polymeric particles have a sphericity of 0.8 or more.

Aspect 4. The injectable particles of aspect 1, wherein the first and second groups of polymeric particles are porous.

Aspect 5. The injectable particles of aspect 1, wherein the first and second groups of polymeric particles are biostable.

Aspect 6. The injectable particles of aspect 1, wherein the first and second groups of polymeric particles are bioresorbable.

Aspect 7. The injectable particles of aspect 1, wherein the first and second groups of polymeric particles are hydrogel particles.

Aspect 8. The injectable particles of aspect 1, wherein the first and second groups of polymeric particles comprise a crosslinked particle-forming polymer that comprises vinyl alcohol monomer.

Aspect 9. The injectable particles of aspect 1, wherein the first and second groups of polymeric particles comprise a crosslinked particle-forming polymer that comprises vinyl alcohol monomers, vinyl ester monomers, and vinyl formal monomers.

Aspect 10. The injectable particles of aspect 1, wherein the first and second polymeric particles are the same and the first and second therapeutic agents are different.

Aspect 11. The injectable particles of aspect 10, wherein the first therapeutic agent is selected from pain-killing agents and anti-angiogenesis agents and wherein the second therapeutic agent is selected from toxins, antineoplastic agents, ablation agents, proinflanimatory agents, sclerosing agents, antibiotic agents and antimicrobial agents.

Aspect 12. The injectable particles of aspect 1, wherein the first and second polymeric particles are different and the first and second therapeutic agents are the same therapeutic agent.

Aspect 13. The injectable particles of aspect 12, wherein said same therapeutic agent has a charge, wherein the first polymeric particles comprise functional groups having a charge that is opposite in sign to the charge of said same therapeutic agent and wherein the second group of polymeric particles do not comprise said functional groups.

Aspect 14. The injectable particles of aspect 13, wherein the first polymeric particles comprise functional groups selected from —COO$^-$ groups, —SO$_3^-$ groups, —NH$_3^+$ groups and =NH$_2^+$ groups.

Aspect 15. The injectable particles of aspect 12, wherein after a period of 12 hours in phosphate buffered saline (PBS) with 0.05% wt/vol polysorbate 20 surfactant, pH 7.4, the percentage of the first therapeutic agent released by the First group of injectable particles is at least 5 times greater than the percentage of the second therapeutic agent released by the second group of injectable particles.

Aspect 16. The injectable particles of aspect 1, wherein the first and second polymeric particles are different and the first and second therapeutic agents are different.

Aspect 17. The injectable particles of aspect 16, wherein the first therapeutic agent is selected from pain-killing agents and anti-angiogenesis agents and wherein the second therapeutic agent is selected from toxins, antineoplastic agents, ablation agents, proinflammatory agents, sclerosing agents, antibiotic agents and antimicrobial agents.

Aspect 18. The injectable particles of aspect 16, wherein after a period of 12 hours in phosphate buffered saline (PBS) with 0.05% wt/vol polysorbate 20 surfactant, pH 7.4, die percentage of the first therapeutic agent released by die first group of injectable particles is at least 5 times greater than the percentage of the second therapeutic agent released by the second group of injectable particles.

Aspect 19. The injectable particles of aspect 1, wherein the first and second groups of injectable particles further comprise a tonicity adjusting agent.

Aspect 20. The injectable particles of aspect 1, wherein the first and second groups of injectable particles are disposed in a single container.

Aspect 21. The injectable particles of aspect 1, wherein the first and second groups of injectable particles are disposed in separate containers.

EXAMPLE

In this example, fast and slow releasing doxorubicin HCl PVA-based microspheres are created. The fast releasing microspheres are produced by exposing 100 mg dry (lyophilized) Contour SE (CSE) microspheres to a solution of doxorubicin HCl in saline (concentration, 2 mg/ml), whereby the doxorubicin is incorporated into the microspheres. As seen from FIG. 1, these doxorubicin HCl loaded microspheres display a "burst" release when tested under in vitro drug release conditions, i.e. 85-95% of the loaded drug is released in 2 hrs in phosphate buffered saline (PBS) with Tween® 20 (polysorbate 20) surfactant (pH 7.4, 0.05% wt/vol polysorbate 20) (see top curve in FIG. 1). The slow releasing doxorubicin HCl PVA based microspheres are produced by introducing ionic group substituted polymers, specifically, poly(sodium styrene-4-sulfonate) (Sigma-Aldrich, USA) and poly(vinyl sulfonic acid, sodium salt) (Sigma-Aldrich, USA) into the CSE microspheres by radiation grafting. In particular, 500 mg dry (lyophilized) microspheres were incubated with 5 ml of polymer solution (1% by weight polymer in DI Water) at 37° C. and 100 RPM on an incubator-shaker, followed by e-beam sterilization of nitrogen purged samples at a dose of 25 KGY. The e-beam sterilized microspheres were washed several times (10 times) with D1 water or until neutral pH=7 was attained, followed by lyophilization of the microspheres for 24 hrs. Analogous to the fast releasing microspheres, the slow releasing microspheres are produced by exposing 100 mg dry (lyophilized) microspheres to a solution of doxorubicin HCl in saline (concentration, 2 mg/ml), whereby the doxorubicin is incorporated into the microspheres. From the bottom two curves in FIG. 1, it can be seen that PVA microspheres grafted with ionic polymers (Prototype I, prepared by using 1% solution of poly(sodium styrene-4-sulfonate), and Prototype II, prepared by using 1% solution of poly(vinyl sulfonic acid, sodium salt) display a very controlled, slow and uniform release of the doxorubicin, i.e. only 5% of doxorubicin is released in 2 hrs and only 10% is released in 24 hrs.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. Injectable particles comprising (a) a first group of injectable particles comprising first polymeric particles that comprise a crosslinked particle-forming polymer comprising vinyl alcohol monomer and a charged polymer comprising —SO$_3^-$ groups covalently bound to the particle-forming polymer, said first group of injectable particles being loaded with doxorubicin HCl and (b) a second group of injectable particles comprising second polymeric particles that comprise a crosslinked particle-forming polymer comprising vinyl alcohol monomer, said second group of injectable particles being loaded with doxorubicin HCl, wherein said second group of polymeric particles do not comprise functional groups having a charge, and wherein after a period of 12 hours in phosphate buffered saline (PBS) with 0.05% wt/vol polysorbate 20 surfactant, pH 7.4, a percentage of doxorubicin HCl released by said second group of injectable particles is at least 5 times greater than a percentage of doxorubicin HCl released by said first group of injectable particles.

2. The injectable particles of claim 1, wherein 95 vol % of said first and second groups of polymeric particles have a longest linear cross-sectional dimension between 40 μm and 5000 μm.

3. Injectable particles comprising (a) a first group of injectable particles comprising first polymeric particles that comprise a crosslinked particle-forming polymer comprising vinyl alcohol monomer and a charged polymer comprising —SO$_3^-$ groups covalently bound to the particle-forming polymer, said first group of injectable particles being loaded with doxorubicin HCl and (b) a second group of injectable particles comprising second polymeric particles that comprise a crosslinked particle-forming polymer comprising vinyl alcohol monomer, said second group of injectable particles being loaded with doxorubicin HCl, wherein said second group of polymeric particles do not comprise functional groups having a charge, and wherein a percentage of doxorubicin HCl released by said second group of injectable particles is 85-95% after a period of 2 hours in phosphate buffered saline (PBS) with 0.05% wt/vol polysorbate 20 surfactant, pH 7.4, and wherein a percentage of doxorubicin HCl released by said first group of injectable particles is about 10% after a period of 24 hours in phosphate buffered saline (PBS) with 0.05% wt/vol polysorbate 20 surfactant, pH 7.4.

* * * * *